(12) United States Patent
Noda

(10) Patent No.: US 7,001,418 B2
(45) Date of Patent: Feb. 21, 2006

(54) INTRAVASCULAR HEAT EXCHANGE CATHETER WITH INSULATED COOLANT TUBES

(75) Inventor: Wayne Arthur Noda, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 478 days.

(21) Appl. No.: 10/427,011

(22) Filed: Apr. 30, 2003

(65) Prior Publication Data

US 2004/0220647 A1    Nov. 4, 2004

(51) Int. Cl.
*A61F 7/12*    (2006.01)

(52) U.S. Cl. ...................................... 607/105; 607/104
(58) Field of Classification Search ......... 607/104–106
See application file for complete search history.

(56) References Cited

U.S. PATENT DOCUMENTS

| | | | | |
|---|---|---|---|---|
| 3,971,383 A | * | 7/1976 | van Gerven | 606/23 |
| 4,111,209 A | * | 9/1978 | Wolvek et al. | 607/105 |
| 4,881,576 A | * | 11/1989 | Kitami et al. | 138/125 |
| 5,110,721 A | * | 5/1992 | Anaise et al. | 435/1.2 |
| 5,400,602 A | * | 3/1995 | Chang et al. | 62/50.7 |
| 5,452,582 A | * | 9/1995 | Longsworth | 62/51.2 |
| 5,647,051 A | * | 7/1997 | Neer | 388/811 |
| 6,059,768 A | * | 5/2000 | Friedman | 604/523 |
| 6,149,677 A | * | 11/2000 | Dobak, III | 607/106 |
| 6,379,348 B1 | * | 4/2002 | Onik | 606/21 |
| 2003/0139791 A1 | * | 7/2003 | Dobak | 607/105 |
| 2003/0225442 A1 | * | 12/2003 | Saadat | 607/105 |

FOREIGN PATENT DOCUMENTS

GB    2136528 A    *  9/1984

* cited by examiner

*Primary Examiner*—Linda C M Dvorak
*Assistant Examiner*—Henry M Johnson, III
(74) *Attorney, Agent, or Firm*—John L. Rogitz

(57) ABSTRACT

Various types of insulated coolant lines that extend between a heat exchanger and an intravascular heat exchange catheter are disclosed.

5 Claims, 2 Drawing Sheets

INTRAVASCULAR HEAT EXCHANGE CATHETER WITH INSULATED COOLANT TUBES

FIELD OF THE INVENTION

The present invention relates generally to intravascular heat exchange catheters.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

As recognized by the present invention, condensation can accumulate on the fluid lines (typically IV tubes) that carry cold circulating coolant between the catheter and heat exchanger. This condensation is undesirable because it can lead to messy dripping water near the patient or onto electrical equipment. Furthermore, heat is exchanged with the coolant as it flows through the lines. This means that the lines represent an undesirable parasitic heat load (adding heat to the coolant) when the coolant is desired to be as cold as possible. On the other hand, when it is desired to warm a patient, the coolant when hotter than room temperature will undesirably lose heat as it flows through the lines. Having recognized these problems, the solution below is provided.

SUMMARY OF THE INVENTION

A system for establishing human patient temperature includes a heat exchange catheter configured for placement in the patient to exchange heat therewith when coolant is circulated through the catheter, and a heat exchanger supplying coolant to the catheter and receiving coolant from the catheter in a closed circuit. The closed circuit includes at least one thermally insulated coolant line.

In a preferred embodiment, the thermally insulated coolant line includes an inner tube forming a lumen for carrying coolant and an outer insulating tube, with the inner tube being closely received in the outer insulating tube such that no space exists between the tubes. The inner tube can be made of IV tubing and the outer tube can be made of closed-cell foam or a metallic foil-like material.

In an alternate preferred embodiment, the coolant line includes an inner tube forming a coolant-carrying lumen and an outer tube surrounding the inner tube and spaced therefrom by webs that connect the inner tube to the outer tube such that at least one insulative dead air pocket is formed between the inner and outer tubes. The inner tube, outer tube, and web can be made of a single unitary structure, or the outer tube can be made of a separate structure than the inner tube.

In another alternate embodiment, the coolant line includes an inner tube forming a coolant-carrying lumen and a substantially incompressible spacer on an outer surface of the inner tube. An outer tube surrounds the spacer such that at least one dead air pocket is established between the tubes. The spacer may be a helically configured monofilament. If desired, the dead air pocket can have proximal and distal ends that are sealed.

In another aspect, a method for treating a patient includes providing a heat exchanger, and advancing a heat exchange catheter into the patient. The catheter communicates with the heat exchanger. The method also includes circulating coolant between the heat exchanger and catheter such that heat is exchanged between the catheter and patient without infusing coolant into the bloodstream of the patient. At least one coolant line between the catheter and heat exchanger is thermally insulated.

In still another aspect, in a system including a heat exchanger, an intravascular closed loop heat exchange catheter, and at least one coolant line connecting the heat exchanger to the catheter, means are provided for insulating the coolant line.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
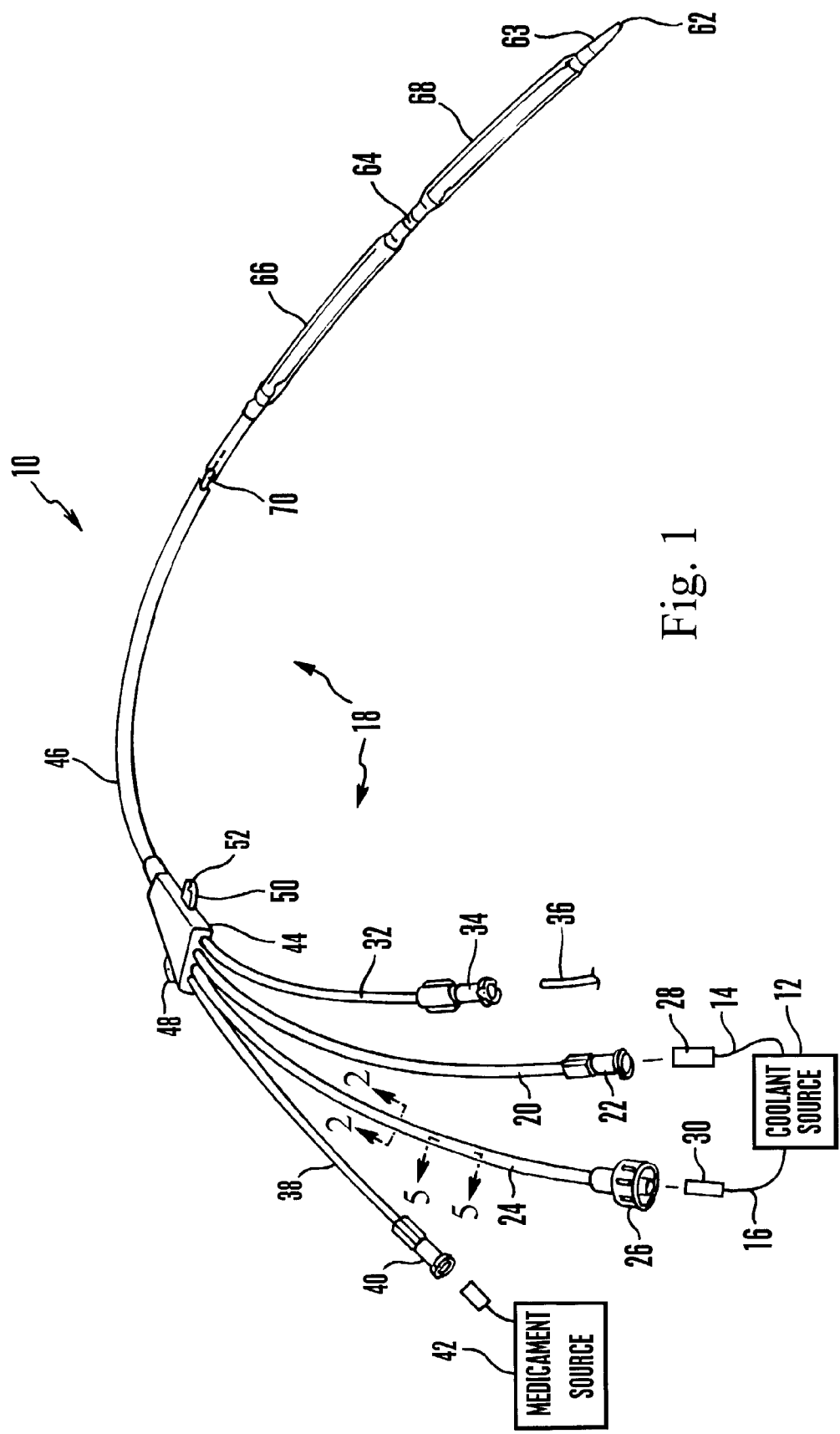
FIG. 1 is a perspective view of the present intravascular heat exchange catheter, schematically showing a medicament source and coolant source in an exploded relationship with the catheter.

Referring initially to FIG. 1, a therapeutic catheter system, generally designated 10, is shown for establishing and maintaining hypothermia in a patient, or for attenuating a fever spike in a patient and then maintaining normal body temperature in the patient. Commencing the description of the system 10 at the proximal end, as shown the system 10 includes a coolant source 12 that can be a water-bath heat exchange system or a TEC-based heat exchange system such as any of the systems disclosed in one or more of the above-referenced patents. In any case, the coolant source provides warmed or cooled coolant such as saline through a coolant supply line 14, and coolant is returned to the source 12 via a coolant return line 16. A catheter, generally designated 18, includes a source tube 20 terminating in a fitting such as a female Luer fitting 22. Also, the catheter 18 has a return tube 24 terminating in a fitting such a male Luer fitting 26. The fittings 22, 26 can be selectively engaged with complementary fittings 28, 30 of the lines 14, 16 to establish a closed circuit coolant path between the catheter 18 and coolant source 12. One or all of the lines 14, 16, 20, 24 are insulated in accordance with principles set forth below. The catheter 18 may be any one of the catheters set forth in the above-referenced patents. An exemplary catheter is set forth herein for illustration purposes.

Additionally, the catheter 18 includes a guide wire and primary infusion tube 32 that terminates in a fitting such as a female Luer 34. A guide wire 36 can be advanced through the tube 32 in accordance with central venous catheter placement principles, or medicament or other fluid can be infused through the guide wire and primary infusion tube 32. Moreover, a secondary infusion tube 38 with female Luer fitting 40 can be selectively engaged with a medicament source 42 for infusing fluid from the source 42 through the secondary tube 38.

As discussed further below, the tubes 20, 24, 32, 38 are held in a distally-tapered connector manifold 44. As also set forth further below, the connector manifold 44 establishes respective pathways for fluid communication between the tubes 20, 24, 32, 38 and respective lumens in a catheter body 46.

A suture anchor 48 advantageously is formed on the connector manifold 44 for suturing the catheter 18 to a patient in accordance with central venous catheter operating principles. In one intended environment, the suture anchor 48 includes opposed ears 50 formed with respective suture holes 52. Other equivalent anchor structure can be used to hold the catheter 18 onto the patient, however, including surgical tape. When the catheter is a so-called Swan-Ganz catheter, i.e., a catheter of the type disclosed in U.S. Pat. No. 3,995,623, incorporated herein by reference, the anchor 48 typically would not be provided.

The catheter body 46 may include at least two lumens, and in the preferred embodiment the catheter body 46 includes at least four lumens. More specifically, the catheter body 46 can define a coolant supply lumen, a coolant return lumen, a guide wire lumen, and a secondary infusion lumen. A lumen can also be provided for holding a wire or wires that are attached to one or more distally-located sensors, such as temperature sensors, pressure sensors, gas sensors, and electrical sensors.

In any case, the connector manifold 44 establishes a pathway for fluid communication between the coolant supply tube 20 and the coolant supply lumen of the catheter. Likewise, the connector manifold 44 establishes a pathway for fluid communication between the coolant return tube 24 and the coolant return lumen. Further, the connector manifold 44 establishes a pathway for fluid communication between the guide wire and primary infusion tube 32, and the guide wire lumen, which can terminate at an open distal hole 62 defined by a distally tapered and chamfered distal tip 63 of the catheter body 46. Also, the connector manifold 44 establishes a pathway for fluid communication between the secondary infusion tube 38 and the secondary infusion lumen, which can terminate at an infusion port 64 in a distal segment of the catheter body 46. Additional ports can be provided along the length of the catheter.

The catheter 18 has a distally-located heat exchange member for effecting heat exchange with blood as it flows past the catheter when the catheter is positioned in the vasculature of a patient. The heat exchange member can be any of the heat exchange members disclosed in the above-referenced patents. By way of example, the preferred non-limiting catheter shown in FIG. 1 can have proximal and distal thin-walled heat exchange membranes 66, 68 that are arranged along the last fifteen or so centimeters of the catheter body 46 and that are bonded to the outer surface of the catheter body 46, with the infusion port 64 being located between the heat exchange membranes 66, 68. Thus, each preferred non-limiting heat exchange membrane is about six centimeters to seven and one-half centimeters in length, with the heat exchange membranes being longitudinally spaced from each other along the catheter body 46 in the preferred embodiment shown. Essentially, the heat exchange membranes 66, 68 extend along most or all of that portion of the catheter 46 that is intubated within the patient. The heat exchange membranes can be established by a medical balloon material.

The heat exchange membranes 66, 68 can be inflated with coolant from the coolant source 12 as supplied from the coolant supply lumen, and coolant from the heat exchange membranes 66, 68 is returned via the coolant return lumen to the coolant source 12. In their inflated configurations, the heat exchange membranes define a diameter of about ten French, and preferably no more than twelve French. Thus, the heat exchange membranes 66, 68 are relatively long and comparatively thin, to advantageously avoid excessively blocking blood flow through the vena cava while nevertheless effecting patient cooling.

If desired, a temperature sensor 70 such as a thermistor or other suitable device can be attached to the catheter 18 as shown. The sensor 70 can be mounted on the catheter 18 by solvent bonding at a point that is proximal to the membranes 66, 68. Or, the sensor 70 can be disposed in a lumen of the catheter 18, or attached to a wire that is disposed in a lumen of the catheter 18, with the sensor hanging outside the catheter 18. Alternatively, a separate temperature probe can be used, such as the esophageal probe disclosed in U.S. Pat. No. 6,290,717, incorporated herein by reference. As yet another alternative, a rectal probe or tympanic temperature sensor can be used. In any case, the sensor is electrically connected to the coolant source 12 for control of the temperature of the coolant as described in various of the above-referenced patents.

As envisioned by the present invention, the structure set forth above can be used in many medical applications to cool a patient and/or to maintain temperature in a normothermic or hypothermic patient, for purposes of improving the medical outcomes of patients on whom, e.g., aneurysm surgery is to be performed, preferably while the patient's temperature is below normal body temperature. The structure can then be used to rewarm the patient in a controlled manner by circulating warm coolant through the structure, or by otherwise regulating natural body rewarming by circulating coolant that is maintained at an appropriate cool (relative to normal body temperature) or warm (relative to normal body temperature) temperature through the structure.

As another example, head trauma and/or stroke can be treated by and after lowering and maintaining the patient's temperature below normal body temperature. Or, cardiac arrest can be treated while the patient's temperature is below normal body temperature. Yet again, minimally invasive heart surgery can be performed on the patient while the patient's temperature is below normal body temperature. And, myocardial infarction in the patient can be treated while the patient's temperature is below normal body temperature. Also, the present invention understands that for certain patients, e.g., stroke victims, it is important to maintain the temperature of a patient at or below normal body temperature, when the patient runs or attempts to run a fever. For severe ischemic stroke victims, the malady can be treated by maintaining the patients body temperature at a hypothermic level.

Figure 2:
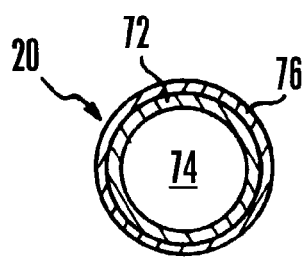
FIG. 2 is a cross-section of a first embodiment of an insulated coolant line, as seen along the line 2—2 in FIG. 1.

Now referring to FIGS. 2–5, details of various insulation methods for one or more of the tubes 14, 16, 20, and 24 can be seen. In FIG. 2, taking the coolant source tube 20 as an example with the understanding that the discussion below can also apply to the tubes 14, 16, and 24, the coolant supply tube 20 can have an inner tube 72 made of IV tubing material such as Tygon polyvinylchloride (PVC) that forms a lumen 74 for carrying coolant. The inner tube 72 is closely received in an outer insulating tube 76 such that substantially no space exists between the tubes. The outer insulating tube 76 can be made of closed-cell foam. In an alternate embodiment, the outer tube 76 can be made of a metallic, foil-like material such as Mylar to provide a radiation barrier in addition to providing a convective heat transfer barrier.

Figure 3:
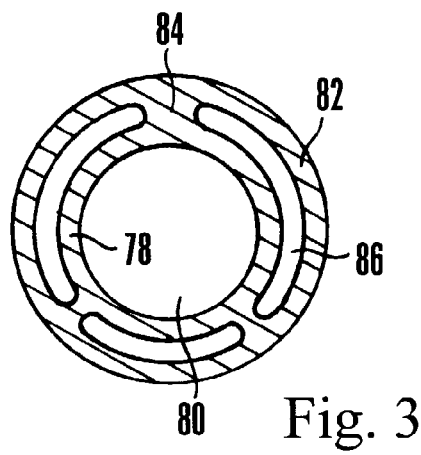
FIG. 3 is a cross-section of a second embodiment of an insulated coolant line, as seen along the line 2—2 in FIG. 1.

FIG. 3 shows an insulated unitary tube structure that can be used for any one or more of the tubes 14, 16, 20, and 24 shown in FIG. 1. An inner tube 78 forms a coolant-carrying lumen 80. An outer tube 82 surrounds the inner tube 78 and is spaced therefrom. One or more webs 84 connect the inner tube 78 to the outer tube 82 as shown. With this structure, insulative dead air pockets 86 are formed between the inner and outer tubes 78, 82. If desired, the distal and proximal open ends (not shown) of the dead air pockets 86 may be sealed. If that is the case, one or more small vent holes may be formed in the outer tube 82 or sealed ends of each dead air pocket to equalize pressure in the dead air pockets 86. The unitary tube structure shown in FIG. 3 may be made by extrusion and may be made of IV line material/PVC.

Figure 4:
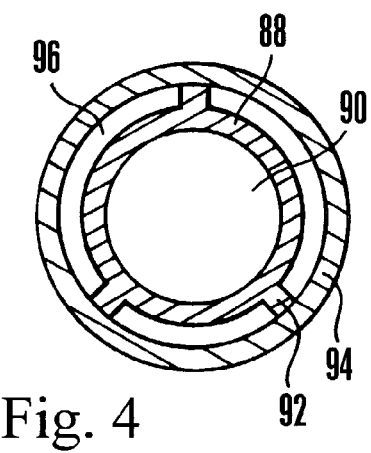
FIG. 4 is a cross-section of a third embodiment of an insulated coolant line, as seen along the line 2—2 in FIG. 1.

In contrast, FIG. 4 shows a two-piece tube structure that is in all essential respects identical to the tube structure shown in FIG. 3, except that an inner tube 88 forming a lumen 90 and spacer webs 92 is formed by, e.g., extrusion as one piece, while an outer tube 94 is formed as a second piece for ease of manufacture and then disposed around the inner tube 88. Insulative dead air pockets 86 are formed between the inner and outer tubes. Both the structures shown in FIGS. 3 and 4 may be made of Tygon PVC tubing or other flexible plastic IV-type tubing.

Figure 5:
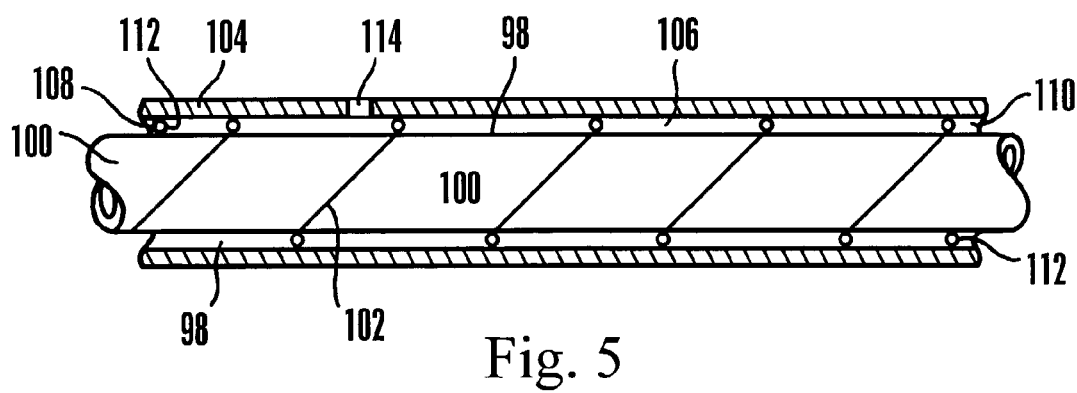
FIG. 5 is a partial cross-section of a fourth embodiment of an insulated coolant line, as seen along the line 5—5 in FIG. 1.

FIG. 5 shows a tube structure that includes a conventional IV-type inner tube 98 forming a coolant lumen 100. The outside surface of the inner tube 98 bears a helically-configured, substantially incompressible spacer 102. In one non-limiting embodiment, the spacer 102 is monofilament nylon about one-half millimeter in diameter. An outer tube 104 is loosely disposed around the spacer 102 to form a dead air pocket 106 between the tubes 98, 104. As was the case with the structures shown in FIGS. 3 and 4, the proximal and distal ends 108, 110 of the dead air pocket 106 can be sealed with sealant 112, and one or more small vent holes 114 can be formed in the outer tube 104 to equalize pressure in the dead air pocket 106 with ambient pressure.

While the particular INTRAVASCULAR HEAT EXCHANGE CATHETER WITH INSULATED COOLANT TUBES as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

What is claimed is:

1. In a system including a heat exchanger, an intravascular closed loop heat exchange catheter disposable in a patient to exchange heat therewith, and at least one coolant line connecting the heat exchanger to the catheter and located outside the body of the patient when the catheter is disposed inside the patient, means for insulating the coolant line.

2. The system of claim 1, comprising at least one insulated coolant supply line and at least one insulated coolant return line.

3. The system of claim 1, wherein the means for insulating includes an outer insulating tube closely surrounding the coolant line such that no space exists between the tube and line.

4. The system of claim 1, wherein the means for insulating includes outer tube surrounding the coolant line and spaced therefrom by at least one web such that at least one insulative dead air pocket is formed between the coolant line and outer tube.

5. The system of claim 1, wherein the means for insulating includes a substantially incompressible spacer on an outer surface of the coolant line and an outer tube surrounding the spacer such that at least one dead air pocket is established between the outer tube and coolant line.

* * * * *